United States Patent

Vicari et al.

[11] Patent Number: 5,849,972
[45] Date of Patent: Dec. 15, 1998

[54] OLIGOMERIZATION OF OLEFINS TO HIGHLY LINEAR OLIGOMERS, AND CATALYSTS FOR THIS PURPOSE

[75] Inventors: Maximilian Vicari, Neuhofen; Peter Polanek, Weinheim, both of Germany

[73] Assignee: BASF Aktiengesellschaft, Ludwigshafen, Germany

[21] Appl. No.: 646,298

[22] PCT Filed: Nov. 21, 1994

[86] PCT No.: PCT/EP94/03838

§ 371 Date: May 16, 1996

§ 102(e) Date: May 16, 1996

[87] PCT Pub. No.: WO95/14647

PCT Pub. Date: Jun. 1, 1995

[30] Foreign Application Priority Data

Nov. 22, 1993 [DE] Germany .......... 43 39 713.1

[51] Int. Cl.⁶ .......... C07C 2/02; B01J 23/00
[52] U.S. Cl. .......... 585/531; 585/533; 502/74; 502/337
[58] Field of Search .......... 585/531, 533, 585/332, 512; 502/74, 66, 337

[56] References Cited

U.S. PATENT DOCUMENTS

| | | |
|---|---|---|
| 3,557,242 | 1/1971 | Sampson et al. .......... 260/618.3 |
| 3,642,661 | 2/1972 | Jolley et al. . |
| 3,729,428 | 4/1973 | Allum et al. . |
| 3,816,555 | 6/1974 | Allum et al. . |
| 4,029,719 | 6/1977 | Forni et al. . |
| 4,225,743 | 9/1980 | Hoshiyama et al. . |
| 4,436,946 | 3/1984 | Smutny . |
| 4,538,012 | 8/1985 | Miller . |
| 4,542,251 | 9/1985 | Miller . |
| 4,613,580 | 9/1986 | Frame . |
| 4,912,280 | 3/1990 | Clerici . |
| 5,073,658 | 12/1991 | Saleh et al. . |
| 5,108,970 | 4/1992 | Young et al. . |
| 5,113,034 | 5/1992 | Soled et al. . |
| 5,134,242 | 7/1992 | Le et al. . |
| 5,146,030 | 9/1992 | Sanderson . |
| 5,169,824 | 12/1992 | Saleh et al. . |

FOREIGN PATENT DOCUMENTS

| | | |
|---|---|---|
| 202 670 | 11/1986 | European Pat. Off. . |
| 261 730 | 3/1988 | European Pat. Off. . |
| 329 305 | 8/1989 | European Pat. Off. . |
| 2 029 624 | 3/1971 | Germany . |
| 2 051 402 | 5/1971 | Germany . |
| 2 347 235 | 4/1974 | Germany . |
| 28 55 423 | 7/1979 | Germany . |

OTHER PUBLICATIONS

Sbrana et al., Oligomerization of Olefins . . . , LaChim. E L'Industria, v. 56, 1974, 110–116 Feb.
Chem. and Ind, May 1974, IFP Dimersol process for . . . , Chauvin et al, 375–378.
Applied Catalysis, 31 1987, 259–266, Espinoza et al. No month.

*Primary Examiner*—Michael L. Lewis
*Assistant Examiner*—Alexander G. Ghyka
*Attorney, Agent, or Firm*—Keil & Weinkauf

[57] ABSTRACT

Straight-chain $C_2$–$C_6$-olefins are oligomerized to their dimers, trimers and tetramers by means of a fixed-bed catalyst, at superatmospheric pressure and at room temperature or elevated temperatures, by a process in which the catalyst used is one which contains, as active components, after deduction of the loss on ignition following heating at 900° C., from 10 to 70% by weight of nickel oxide, calculated as NiO, from 5 to 30% by weight of titanium dioxide or zirconium dioxide, from 0 to 20% by weight of alumina, from 20 to 40% by weight of silica and from 0.01 to 1% by weight of an alkali metal oxide, with the proviso that the contents of the individual components in the catalyst sum to 100% by weight.

10 Claims, No Drawings

OLIGOMERIZATION OF OLEFINS TO HIGHLY LINEAR OLIGOMERS, AND CATALYSTS FOR THIS PURPOSE

The present invention relates to a process for the oligomerization of olefins of 2 to 6 carbon atoms, and precipitation catalysts for this purpose.

Olefins of 2 to 6 carbon atoms and mixtures thereof, in particular olefins of 4 carbon atoms, are available in large amounts both from FCC plants and from steam crackers. The particular $C_4$ cut, ie. the mixture of butenes and butanes, is very suitable for the preparation of oligomers, in particular octenes and dodecenes, after separation of the isobutene. After hydroformylation and subsequent hydrogenation to the corresponding alcohols, both the octenes and dodecenes can be used, for example, for the preparation of plasticizers.

With regard to the use as a plasticizer alcohol, the degree of branching plays a decisive role with respect to the properties of the plasticizer. The degree of branching is described by the ISO index, which specifies the average number of methyl branches in the particular fraction.

For example, n-octenes with 0, methylheptenes with 1 and dimethylhexenes with 2 contribute to the ISO index of a $C_8$ fraction. The lower the ISO index, the more linear are the molecules in the particular fraction. The higher the linearity, ie. the lower the ISO index, the higher are the yields in the hydroformylation and the better are the properties of the plasticizer prepared therewith. A lower ISO index, for example in the case of phthalate plasticizers, has an advantageous effect in terms of low volatility and better brittleness temperature of the flexible PVC produced using the plasticizer. Slightly branched oligomers of lower olefins are obtainable from reactions of both homogeneous and heterogeneous catalysts which contain predominantly nickel as the active component. However, other catalytically active metals, such as ruthenium (G. Braca, La Chimica e l'Industria, 56 (1974), 110–116), palladium, according to U.S. Pat. No. 4,436,946, and copper, cobalt, iron, chromium and titanium, according to GB 824 002, have also been described. Only the nickel-containing catalysts have become industrially important.

DE 28 55 423 discloses, as a homogeneous catalyst, a system which consists of the nickel(II) salt of octanoic acid, ethylaluminum dichloride and a free fatty acid. A catalyst system of this type is also used in the only homogeneously catalyzed process of industrial importance for olefin oligomerization (Y. Chuvin, Chemistry and Industry, 1974, 375–378).

Homogeneously catalyzed processes for the oligomerization of olefins present problems on the one hand owing to the removal of the catalyst and on the other hand owing to the substantially higher catalyst costs per ton of product in comparison with a procedure catalyzed by heterogeneous catalyst. In the removal and destruction of the catalyst, which is fed through the plant in a straight pass with the stream of starting materials, wastewater containing heavy metals and ammonium is also formed and has to be appropriately worked up and disposed of.

In addition to the homogeneous catalysts, a large number of heterogeneous catalyst systems based on nickel and silicon, which often additionally contain aluminum and are prepared by a wide range of methods, have also been described.

U.S. Pat. No. 5,169,824 discloses, for example, the preparation of a nickel precipitation catalyst on $Al_2O_3/SiO_2$. The NiO content is adjusted so that the $Al_2O_3/SiO_2$ carrier is covered with one layer, ie. from 0.07 to 0.12% by weight of NiO per 1 $m^2$ of carrier surface.

Under conditions which are supercritical for the starting olefin trans-2-butene and with the addition of decane as a subcritical solvent, this catalyst gives a conversion in the autoclave of 86%, a $C_8$ selectivity of 53% and an ISO index of 1.3 in the $C_8$ fraction.

According to DD 273 055, nickel and aluminum are precipitated onto $SiO_2$. With a hydrogen-saturated butene/butane mixture, a conversion of 57% to oligomers is achieved with 91% $C_8$ selectivity and an ISO index of 1.2.

According to DE 20 51 402, a catalyst for the codimerization of propylene and n-butenes can be obtained by coprecipitation, starting from a silica sol, a nickel salt and colloidal alumina.

According to EP 202 670, a catalyst having oligomerization activity can be prepared by impregnating alumina moldings with a nickel salt, calcining the product and activating it by impregnation with aluminum chloride and diethylaluminum chloride.

Other catalysts can be obtained by exchanging the positively charged particles present on the carrier surface, such as protons or alkali metal or alkaline earth metal ions, for nickel ions. A very wide range of carriers are used, for example according to R. Espinoza, Appl. Catal. 31 (1987), 259–266, amorphous aluminum silicate, according to EP 261 730, Y zeolite exchanged with Fe, Cu, La, Ca, Ni or Co, according to NL 8 500 459, zeolites of the ZSM type, according to DE 2 347 235, an X zeolite, or according to U.S. Pat. No. 5,134, 242, a zeolite having the MCM-41 structure or a nick-el-containing zeolite prepared from Cs- or Ba-exchanged CZS-1 or ultrastable high-Si faujasite according to EP 329 305.

In addition to these catalysts mentioned as examples, other catalysts described are, for example, those based on halogen-free titanium salts or zirconium salts on clay, according to U.S. Pat. No. 5,146,030, and catalysts having a disperse $TiO_2$ phase on a carrier comprising $Al_2O_3$ covered with one $SiO_2$ layer, according to U.S. Pat No. 5,073,658.

Furthermore, U.S. Pat. No. 5,113,034 describes catalysts based on $NiO/ZrO_2/SO_4/SiO_2$ or $TiO_2/SO_4$ for the oligomerization of propene and butenes.

Owing to the high acidity of the carrier, highly branched oligomers are obtained with the catalysts, for example those based on zeolite, or superacidic catalysts, such as $ZrO_2/SO_4$ or $TiO_2/SO_4$.

In the case of high acidity of the catalyst, the oligomerization takes place via a cationic mechanism which, when butenes are used as the starting material, inevitably proceeds via the more stable 2-butyl cation, for the most part to dimethylhexenes and methylheptenes.

However, as explained above, very high linearity of the oligomers, ie. a low ISO index (not more than 1–1.2), is required for the preparation of plasticizers, in order to obtain high quality plasticizers.

Highly linear olefins are obtained if the oligomerization takes place via a coordination mechanism. Only via the coordination mechanism is it possible to obtain n-octenes which by definition contribute by the factor 0 to the ISO index of the $C_8$ fraction.

In order to be able to utilize the considerable heat of reaction generated in the oligomerization, for example to use the heat of reaction for the downstream separation columns, it is advantageous to carry out the oligomerization above a reactor temperature of 160° C. and at a supercritical pressure with respect to the butene/butane mixture, for example the butene/butane mixture used being in the supercritical state.

The high reactor temperature sets particular requirements for the catalyst, which may be summarized essentially in three aspects:

1. Prevention of the formation of higher oligomers, which adhere to the active surface of the catalyst as a coke intermediate.
2. High stability of the finely divided NiO phase to agglomeration.
3. High stability of the active NiO phase to reduction.

Accordingly, we have found a process for the oligomerization of straight-chain $C_2$–$C_6$-olefins to their dimers, trimers and tetramers by means of a fixed-bed catalyst, at superatmospheric pressure and at room temperature or elevated temperatures, wherein the catalyst used is one which contains, as active components, after deduction of the loss on ignition following heating at 900° C., from 10 to 70% by weight of nickel oxide, calculated as NiO, from 5 to 30% by weight of titanium dioxide and/or zirconium dioxide, from 0 to 20% by weight of alumina, from 20 to 40% by weight of silica and from 0.01 to 1% by weight of an alkali metal oxide, with the proviso that the contents of the individual components in the catalyst sum to 100% by weight.

In a preferred embodiment, the oligomerization is carried out under supercritical conditions with respect to the starting material, preferably without the use of additional solvents which are not in the supercritical state.

According to the invention, the addition of solid $TiO_2$ and/or $ZrO_2$ results in the nickel oxide phase being present in the catalyst in a form which is finely divided and highly stable with regard to reduction to metallic nickel and thus ensuring high activity.

According to U.S. Pat. No. 5,169,824, the formation of higher oligomers can be inhibited by introducing trivalent metal oxides, such as $Al_2O_3$ or $Ga_2O_3$, which produce acidic centers in the catalyst. According to the prior art, the metal oxide may be both coprecipitated with the SiO carrier and introduced into the catalyst carrier by impregnation. In order to obtain oligomers having very high linearity, the introduction and the amount of the metal oxide must be tailored so that, on the one hand, the formation of higher oligomers is inhibited and, on the other hand, the acidity of the carrier does not become too great. This ensures that the reaction occurs preferentially by a coordination mechanism.

According to the invention, a minimum required carrier acidity can be established in the case of simultaneous precipitation of the metal salt solution and the aluminum salt, so that highly linear oligomers can also be obtained when the oligomerization catalyst has high activity.

We have furthermore found that, in the preparation of an oligomerization catalyst which contains the oxides of nickel, silicon, if required aluminum and titanium and/or zirconium or oxides of the two last-mentioned metals, particularly advantageous results are achieved in terms of the desired properties if, in the precipitation of the metal salt solution with alkali metal carbonate solution, on the one hand the titanium-containing or zirconium-containing component is initially taken as solid titanium dioxide or zirconium dioxide or zirconium hydroxide, respectively, and, on the other hand, the aluminum component is coprecipitated with the metal salt solution. After the precipitation, the suspension obtained is filtered, washed, dried and heated.

With regard to the properties of the oligomer mixture, particularly advantageous results are obtained if the precipitation is carried out at, in general, 30°–90° C. and a pH of, in general, 5–9, preferably 6.5–7.5, and the heating is effected at, in general, 350°–650° C., preferably 450°–550° C. After the heating, the catalyst material consists of 5–30% by weight of titanium dioxide and/or zirconium dioxide, 0–20% by weight of alumina and 10–70% by weight of nickel oxide, calculated as NiO, the remainder being silica.

The process for the preparation of the novel oligomerization catalyst is carried out specifically, for example, by initially taking alkali metal waterglass, preferably sodium waterglass, in aqueous solution as a mixture with solid titanium dioxide and, at essentially constant pH, mixing the metal salt solution which contains the amounts of metal salt corresponding to the required amount of nickel and aluminum with the alkali metal carbonate solution, the metals being precipitated in the form of a mixture of metal hydroxides and metal carbonates. The metal salts used are preferably the nitrates, sulfates or acetates of the metals. The metal salt content of the metal salt solutions is, in general, 30–40% by weight of nickel salt and, if required, 10–15% by weight of aluminum salt. The alkali metal carbonate solution is, in general, 15–25, preferably 18–22, % strength by weight. The precipitation is carried out at, in general, 30°–90° C., preferably 60°–80° C., and at a pH of 5–9, preferably 6.5–7.5. The suspension obtained is filtered and is washed until anions of the precipitated metal salts are no longer detectable. Drying is then carried out for example at 150° C. in a drying oven or in a spray dryer. The dried filter cake is heated at, in general, from 350° to 650° C., preferably from 400° to 600° C., for example in a muffle furnace or rotating tube.

The resulting catalyst material, which exhibits a loss on ignition of from about 5 to 15% by weight on heating at 900° C., contains, after deduction of the loss on ignition, from 5 to 30, preferably from 10 to 20, % by weight of titanium dioxide, from 0 to 20, preferably from 0.5 to 10, % by weight of alumina and from 10 to 70, preferably from 40 to 60, % by weight of nickel oxide, calculated as NiO, as the main constituent, the remainder to 100% being silica. In general, this silicon dioxide content is from 20 to 40% by weight. As a consequence of the preparation procedure, the catalyst generally still contains from 0.01 to 1% by weight, preferably from 0.1 to 0.3% by weight, of the alkali metal used for the precipitation, calculated as alkali metal oxide. Observance of this alkali metal content has an advantageous effect on the activity and selectivity of the catalyst.

Before being used, this catalyst material is pelletized or extruded in the conventional manner. For example, the catalyst material is compressed using a pelletizing aid, preferably graphite or stearic acid, to give pellets having, for example, the dimensions 3 mm height×3 mm diameter, 5×5 mm or having, for example, an external diameter of 7 mm, a height of 5 mm and a hole diameter of 3 mm. If stearic acid is used as the pelletizing aid, it is advantageous to heat the catalyst moldings again at from 350° to 650° C., preferably from 400° to 600° C., for example in a muffle furnace or rotating tube.

Before being used, the catalysts prepared in this manner are advantageously subjected to conditioning in a dry nitrogen stream, for example at atmospheric pressure and 150°–500° C., preferably 250°–450 ° C., in order to remove any water still present from the catalyst.

The novel catalysts are highly suitable for the oligomerization of butenes in butene/butane mixtures. Advantageous reaction temperatures for the oligomerization of butenes using the novel catalysts are from 20° to 280° C., preferably above 160° C., in particular from 180° to 210° C., and an advantageous reaction pressure is from 10 to 300 bar, preferably from 20 to 300 bar, in particular from 60 to 80 bar. Surprisingly, the novel catalysts when used in the novel process have two optimum operating ranges with respect to the reaction pressure used and the reaction temperature used, namely a) at a pressure of from 10 to 30 bar, in particular from 15 to 25 bar, and at from 20° C. to 140° C., preferably from 40° to 120° C., and b) at a pressure of from 60 to 300 bar, in particular from 60 to 80 bar, and at a temperature of from 160° to 280° C., in particular from 180° to 210° C. The presence of two optimum operating ranges enables the novel catalysts to be used in butene oligomerization plants operated under different process conditions. By means of the novel catalysts, highly linear, dimeric and trimeric olefins can be obtained in high yield.

It is surprising that, in spite of high acidity in the catalyst due to the doping with alumina, high linearity of the dimer and trimer fraction is obtained.

EXAMPLE 1

902.9 g of $Ni(NO_3)_2 * 6 H_2O$ (corresponding to 225 g of NiO) are dissolved in demineralized water and made up to 3000 ml (metal salt solution). 2000 ml of demineralized water are initially taken in a stirred vessel and 60.7 g of finely divided titanium dioxide powder (corresponding to 58.5 g of pure (100%) $TiO_2$) and 616 g of sodium waterglass solution (corresponding to 166.5 g of $SiO_2$) are added while stirring. The batch is heated to 70° C. and the metal salt solution is pumped in while stirring until a pH of 7.0, measured with a glass electrode, has been established. The metal salt solution and 20% strength by weight sodium carbonate solution are then added simultaneously in a continuous stream, the pH of 7.0 measured with the glass electrode being maintained. After complete addition of the metal salt solution, stirring is continued for another hour without the addition of further sodium carbonate solution. The precipitate is filtered off and is washed with demineralized water until the electrical conductivity is less than 30 $\mu S$. The filter cake is then dried at 150° C. in a drying oven or a spray dryer. The hydroxide/carbonate mixture obtained in this manner is then heated at 500° C. for 4 hours. The catalyst thus obtained has the following composition: 50% by weight of NiO, 36.6% by weight of $SiO_2$, 13% by weight of $TiO_2$ and 0.4% by weight of $Na_2O$. The catalyst powder is mixed with 3% by weight of graphite and compressed to give 3×3 mm pellets.

Comparative Example 1

(catalyst without $TiO_2$)

902.9 g of $Ni(NO_3)_2 * 6 H_2O$ (corresponding to 225 g of NiO) are dissolved in demineralized water and made up to 3000 ml (metal salt solution). 2000 ml of demineralized water are initially taken in a stirred vessel and 832 g of sodium waterglass solution (corresponding to 225 g of $SiO_2$) are added while stirring. The batch is heated to 70° C. and the metal salt solution is pumped in while stirring until a pH of 7.0, measured with a glass electrode, has been established. The metal salt solution and 20% strength by weight sodium carbonate solution are then added simultaneously in a continuous stream, the pH of 7.0 measured with the glass electrode being maintained. After complete addition of the metal salt solution, stirring is continued for another hour without the addition of further sodium carbonate solution. The precipitate is filtered off and is washed with demineralized water until the electrical conductivity is less than 30 $\mu S$. The filter cake is then dried at 150° C. in a drying oven or a spray dryer. The hydroxide/carbonate mixture obtained in this manner is then heated at 500° C. for 4 hours. The catalyst thus obtained has the following composition: 50% by weight of NiO, 49.5% by weight of $SiO_2$ and 0.5% by weight of $Na_2O$. The catalyst powder is mixed with 3% by weight of graphite and compressed to give 3×3 mm pellets.

EXAMPLE 2

The procedure is as described in Example 1, except that a solution of 902.9 g of $Ni(NO_3)_2 * 6 H_2O$ (=225 g of NiO),
348.5 g of $Al(NO_3)_3 * 9 H_2O$ (=45 g of $Al_2O_3$),
76.5 g of finely divided titanium dioxide powder (=58.5 g of 100% $TiO_2$) and
450 g of sodium waterglass solution (=121.5 g of $SiO_2$) is used for precipitation and working up is carried out as described there.

The catalyst thus obtained has the following composition: 50% by weight of NiO, 26.7% by weight of $SiO_2$, 10% by weight of $Al_2O_3$, 13% by weight of $TiO_2$ and 0.3% by weight of $Na_2O$. The catalyst powder is mixed with 3% by weight of graphite and compressed to give 3×3 mm pellets.

Comparative Example 2

(Use of solid alumina instead of a coprecipitation of the alumina)

The procedure is as described in Example 1, except that
76.5 g of finely divided titanium dioxide powder (=58.5 g of 100% $TiO_2$),
62.8 g of finely divided boehmite powder (=45 g of 100% $Al_2O_3$) and
450 g of sodium waterglass solution (=121.5 g $SiO_2$) are initially taken.

The catalyst thus obtained has the following composition:
50% by weight of NiO,
26.8% by weight of $SiO_2$,
10% by weight of $Al_2O_3$,
13% by weight of $TiO_2$,
0.2% by weight of $Na_2O$.

The catalyst powder is mixed with 3% by weight of graphite and compressed to give 3×3 mm pellets.

EXAMPLE 3

The following reactions were carried out continuously using a fixed-bed reactor under a pressure which was higher than the autogenous pressure of the butenes and butanes. The pressure was generated by means of the reactor pump upstream of the reactor and was appropriately controlled by pressure relief downstream of the reactor and after cooling of the reaction product. The following conditions were kept constant in the comparative experiments:

Mixture of starting materials:

| | |
|---|---|
| n-butane, isobutane | 33% by weight |
| 1-butene | 11% by weight |
| trans-2-butene | 35% by weight |
| cis-2-butene | 20% by weight |
| isobutene | 1% by weight |
| Space velocity: | 0.5 kg/l per h |

Below, the results of the reaction using the novel catalyst based on $NiO/SiO_2/TiO_2$ and using the comparative catalyst based on $NiO/SiO_2$ according to Example 1 and Comparative Example 1 are compared in order to show the effect of doping with $TiO_2$.

| | | |
|---|---|---|
| Pressure [bar] | 70 | |
| Temperature [°C.] | 190 | |
| Catalyst | according to Example 1 | according to Comparative Example 1 |

-continued

|  |  |  |
|---|---|---|
| Total butene conversion [% by weight] | 53 | 41 |
| $C_8$ [% by weight] | 73 | 78 |
| $C_{12}$ [% by weight] | 20 | 17 |
| $C_{16+}$* [% by weight] | 7 | 5 |
| $C_8$ fraction: |  |  |
| methylhepentenes | 65 | 67 |
| dimethylhexenes | 7 | 9 |
| trimethylpentenes | 1 | 3 |
| n-octenes | 24 | 21 |
| ISO index | 0.85 | 0.94 |

*$C_{16+}$: oligomerization products of 16 or more carbon atoms.

EXAMPLE 4

The novel catalyst according to Example 1, based on 50% by weight of $NiO/37\%$ by weight of $SiO_2/13\%$ by weight of $TiO_2$, gives the following results in a liquid phase and in the supercritical state, based on the butenes and butanes used.

|  |  |  |
|---|---|---|
| Pressure [bar] | 30 | 70 |
| Temperature [°C.] | 80 | 190 |
| Total butene conversion [% by weight] | 54 | 53 |
| $C_8$ [% by weight] | 72 | 73 |
| $C_{12}$ [% by weight] | 20 | 20 |
| $C_{16+}$ [% by weight] | 8 | 7 |
| $C_8$ fraction: |  |  |
| methylhepentenes | 73 | 65 |
| dimethylhexenes | 16 | 7 |
| trimethylpentenes | — | 1 |
| n-octenes | 11 | 24 |
| ISO index | 1.1 | 1.1 |

At virtually the same conversion and same ISO index, twice the amount of the desired n-octenes is obtained.

EXAMPLE 5

The procedure is as described in Example 3, using the catalysts described in Example 2 and Comparative Example 2, and the following result is obtained:

|  |  |  |
|---|---|---|
| Pressure [bar] | 70 |  |
| Temperature [°C.] | 190 |  |
| Catalyst | according to Example 2 | according to Comparative Example 2 |
| Total butene conversion [% by weight] | 78 | 55 |
| $C_8$ [% by weight] | 62 | 70 |
| $C_{12}$ [% by weight] | 25 | 21 |
| $C_{16+}$ [% by weight] | 13 | 9 |
| $C_8$ fraction: |  |  |
| methylhepentenes | 68 | 64 |
| dimethylhexenes | 9 | 9 |
| trimethylpentenes | 2 | 3 |
| n-octenes | 21 | 24 |
| ISO index | 0.92 | 0.91 |

At the same ISO index, a substantially higher conversion is obtained with the novel catalyst.

We claim:

1. A process for the oligomerization of straight-chain $C_2$–$C_6$-olefins to their dimers, trimers and tetramers by means of a fixed-bed catalyst, at superatmospheric pressure and at room temperature or elevated temperatures, wherein the catalyst used is one which contains, as active components, after deduction of the loss on ignition following heating at 900° C., from 10 to 70% by weight of nickel oxide, calculated as NiO, from 5 to 30% by weight of titanium dioxide or zirconium dioxide, from 0 to 20% by weight of alumina, from 20 to 40% by weight of silica and from 0.01 to 1% by weight of an alkali metal oxide, with the proviso that the contents of the individual components in the catalyst sum to 100% by weight.

2. A process as defined in claim 1, wherein the oligomerization in the reaction zone is carried out at supercritical temperature and supercritical pressure of the olefins used and without the use of additional solvents which are not in the supercritical state in the reaction zone.

3. A process as defined in claim 1, wherein $C_4$-olefins are oligomerized and the oligomerization is carried out at from 20° to 280° C. and from 10 to 300 bar.

4. A process as defined in claim 1, wherein $C_4$-olefins are oligomerized and the oligomerization is carried out at from 10 to 30 bar and from 20° to 140° C.

5. A process as claimed in claim 1, wherein $C_4$-olefins are oligomerized and the oligomerization is carried out at from 60 to 300 bar and from 160° to 280° C.

6. A catalyst for the oligomerization of olefins of 2 to 6 carbon atoms as defined in claim 1, consisting essentially of nickel oxide, silica, titanium dioxide or zirconium dioxide and, if required, alumina and containing, after deduction of the loss on ignition following heating at 900° C., from 10 to 70% by weight of nickel oxide, calculated as NiO, from 5 to 30% by weight of titanium dioxide or zirconium dioxide, from 0 to 20% by weight of alumina, from 20 to 40% by weight of silica and from 0.01 to 1% by weight of an alkali metal oxide, with the proviso that the proportions of the individual components sum to 100% by weight, obtainable by precipitating a nickel salt solution which is free of aluminum or contains a dissolved aluminium salt at a pH of from 5 to 9 by the addition of this nickel salt solution to an alkali metal waterglass solution which contains solid titanium dioxide or zirconium dioxide, drying and heating the resulting precipitate at from 350° to 650° C.

7. A catalyst as defined in claim 6, obtainable by precipitation at from 30° to 90° C.

8. A process for the oligomerization of straight-chain $C_2$–$C_6$-olefins to their dimers, trimers and tetramers by means of a fixed-bed catalyst, at superatmospheric pressure and at room temperature or elevated temperatures, wherein the catalyst comprises: nickel oxide, silica, titanium dioxide or zirconium dioxide and, optionally, alumina and containing, after deduction of the loss on ignition following heating at 900° C., from 10 to 70% by weight of nickel oxide, calculated as NiO, from 5 to 30% by weight of titanium dioxide or zirconium dioxide, from 0 to 20% by weight of alumina, from 20 to 40% by weight of silica and from 0.01 to 1% by weight of an alkali metal oxide, with the proviso that the proportions of the individual components sum to 100% by weight, obtained by precipitating a nickel salt solution which is free of aluminum or contains a dissolved aluminum salt at a pH of from 5 to 9 by the addition of this nickel salt solution to an alkali metal waterglass solution which contains solid titanium dioxide or zirconium dioxide, drying and heating the resulting precipitate at from 350° to 650° C.

9. The process of claim 1, wherein the catalyst contains from 5 to 30% by weight of titanium dioxide.

10. The process of claim 1, wherein the catalyst contains from 5 to 30% of zirconium dioxide.

* * * * *

UNITED STATES PATENT AND TRADEMARK OFFICE
CERTIFICATE OF CORRECTION

PATENT NO.: 5,849,972

DATED: December 15, 1998

INVENTOR(S): VICARI et al.

It is certified that error appears in the above-identified patent and that said Letters Patent is hereby corrected as shown below:

Col. 8, claim 5, line 21, "claimed" should be --defined--.

Signed and Sealed this

Eleventh Day of May, 1999

Attest:

Q. TODD DICKINSON

*Attesting Officer*     *Acting Commissioner of Patents and Trademarks*